US011419533B2

(12) United States Patent
Damaser et al.

(10) Patent No.: US 11,419,533 B2
(45) Date of Patent: *Aug. 23, 2022

(54) BLADDER EVENT DETECTION FOR DIAGNOSIS OF URINARY INCONTINENCE OR TREATMENT OF LOWER URINARY TRACT DYSFUNCTION

(71) Applicants: THE CLEVELAND CLINIC FOUNDATION, Cleveland, OH (US); The United States Government as represented by the Department of Veterans Affairs, Washington, DC (US); Case Western Reserve University, Cleveland, OH (US)

(72) Inventors: Margot S. Damaser, Cleveland Heights, OH (US); Swarup Bhunia, Gainesville, FL (US); Robert Karam, Gainesville, FL (US); Steve Majerus, Akron, OH (US); Dennis Bourbeau, Cleveland, OH (US); Hui Zhu, Pepper Pike, OH (US)

(73) Assignees: THE CLEVELAND CLINIC FOUNDATION, Cleveland, OH (US); The United States Government as represented by the Department of Veterans Affairs, Washington, DC (US); Case Western Reserve University, Cleveland, OH (US)

( * ) Notice: Subject to any disclaimer, the term of this patent is extended or adjusted under 35 U.S.C. 154(b) by 708 days.

This patent is subject to a terminal disclaimer.

(21) Appl. No.: 16/360,126

(22) Filed: Mar. 21, 2019

(65) Prior Publication Data
US 2019/0223775 A1 Jul. 25, 2019

Related U.S. Application Data

(63) Continuation of application No. 15/142,704, filed on Apr. 29, 2016, now Pat. No. 10,478,113.
(Continued)

(51) Int. Cl.
A61B 5/00 (2006.01)
A61B 5/20 (2006.01)
(Continued)

(52) U.S. Cl.
CPC .............. *A61B 5/205* (2013.01); *A61B 5/076* (2013.01); *A61B 5/202* (2013.01); *A61B 5/6874* (2013.01);
(Continued)

(58) Field of Classification Search
CPC ......... A61B 5/205; A61B 5/076; A61B 5/202; A61B 5/6874; A61B 5/721; A61B 5/726;
(Continued)

(56) References Cited

U.S. PATENT DOCUMENTS 5,807,278 A * 9/1998 McRae ................. A61B 5/205
600/573
6,561,986 B2 * 5/2003 Baura ................... A61B 5/726
600/526
(Continued)

FOREIGN PATENT DOCUMENTS

WO 2004/047914 A1 6/2004
WO 2008/130467 A1 10/2008

OTHER PUBLICATIONS

European Extended Search Report for corresponding European Application Serial No. 19164995.3, dated Apr. 30, 2019, pp. 1-262.
(Continued)

*Primary Examiner* — May A Abouelela
(74) *Attorney, Agent, or Firm* — Tarolli, Sundheim, Covell & Tummino LLP

(57) ABSTRACT

The present disclosure relates generally to using detected bladder events for the diagnosis of urinary incontinence or the treatment of lower urinary tract dysfunction. A system includes a sensing device comprising a pressure sensor to directly detect a pressure within a bladder. The sensing device is adapted to be located within the bladder. The system also includes a signal processing device to: receive a signal indicating the detected pressure within the bladder; detect a bladder event based the detected pressure within the signal; and characterize the bladder event as a bladder contraction event or a non-contraction event. The characterization of the bladder event can be used in the diagnosis of urinary incontinence or the treatment of lower urinary tract dysfunction.

20 Claims, 16 Drawing Sheets

Related U.S. Application Data

(60) Provisional application No. 62/193,238, filed on Jul. 16, 2015, provisional application No. 62/154,350, filed on Apr. 29, 2015.

(51) Int. Cl.
*A61N 1/36* (2006.01)
*A61B 5/07* (2006.01)
*A61B 5/03* (2006.01)

(52) U.S. Cl.
CPC .............. *A61B 5/721* (2013.01); *A61B 5/726* (2013.01); *A61B 5/7282* (2013.01); *A61N 1/3606* (2013.01); *A61N 1/36007* (2013.01); *A61N 1/36135* (2013.01); *A61N 1/36167* (2013.01); *A61B 5/0031* (2013.01); *A61B 5/03* (2013.01); *A61B 2560/0214* (2013.01); *A61B 2560/0219* (2013.01); *A61B 2562/0247* (2013.01)

(58) Field of Classification Search
CPC ....... A61B 5/7282; A61B 5/0031; A61B 5/03; A61B 2560/0214; A61B 2560/0219; A61B 2562/0247; A61N 1/36007; A61N 1/3606; A61N 1/36135; A61N 1/36167
USPC .................................................. 600/302, 561
See application file for complete search history.

(56) References Cited

U.S. PATENT DOCUMENTS

| | | | | |
|---|---|---|---|---|
| 6,916,283 B2* | 7/2005 | Tracey | .................... | A61B 5/205 600/29 |
| 7,147,606 B1* | 12/2006 | Chang | ................... | A61B 5/0031 600/561 |
| 7,930,034 B2 | 4/2011 | Gerber | | |
| 8,121,691 B2* | 2/2012 | Gerber | ................. | A61N 1/0558 607/41 |
| 8,204,597 B2* | 6/2012 | Gerber | ............... | A61N 1/36007 607/41 |
| 8,295,933 B2* | 10/2012 | Gerber | .................... | A61B 5/205 607/41 |
| 8,323,189 B2* | 12/2012 | Tran | ...................... | A61B 5/1112 600/300 |
| 8,805,508 B2* | 8/2014 | Gerber | ................... | A61B 5/202 607/41 |
| 9,185,489 B2* | 11/2015 | Gerber | .................... | A61B 5/204 |
| 9,327,117 B2* | 5/2016 | Denison | ................ | A61B 5/204 |
| 10,702,200 B2* | 7/2020 | Pop | ................... | A61B 5/14546 |
| 2005/0113878 A1* | 5/2005 | Gerber | ................... | A61N 1/36071 607/39 |
| 2006/0190051 A1* | 8/2006 | Gerber | ............... | A61N 1/36007 607/41 |
| 2006/0264775 A1* | 11/2006 | Mills | .................... | A61B 5/0537 600/547 |
| 2007/0027494 A1* | 2/2007 | Gerber | ................... | A61B 5/686 607/41 |
| 2007/0252713 A1* | 11/2007 | Rondoni | ................. | A61B 5/202 340/573.5 |
| 2007/0252714 A1* | 11/2007 | Rondoni | .............. | A61B 5/0002 340/573.5 |
| 2007/0255176 A1* | 11/2007 | Rondoni | ................. | A61B 5/204 600/573 |
| 2010/0069784 A1* | 3/2010 | Blaivas | ................... | A61B 5/064 600/561 |
| 2010/0121161 A1* | 5/2010 | Robertson | .............. | A61B 5/205 600/302 |
| 2010/0137736 A1* | 6/2010 | Addington | ............. | G16H 40/63 600/546 |
| 2010/0234696 A1* | 9/2010 | Li | ......................... | A61B 5/4875 600/300 |
| 2011/0071366 A1* | 3/2011 | McKenna | .......... | A61B 5/14551 600/300 |
| 2011/0264163 A1 | 10/2011 | Tracey et al. | | |
| 2012/0035496 A1* | 2/2012 | Denison | ............. | A61N 1/36007 600/547 |
| 2012/0150065 A1* | 6/2012 | Clarkson | ............ | A61B 5/02141 600/561 |
| 2012/0172682 A1* | 7/2012 | Linderman | .......... | A61B 5/6806 600/301 |
| 2012/0310051 A1* | 12/2012 | Addison | ................ | A61B 5/726 600/301 |
| 2012/0330373 A1* | 12/2012 | Ternes | ............... | A61N 1/36139 607/42 |
| 2013/0289659 A1 | 10/2013 | Nelson et al. | | |
| 2013/0303942 A1* | 11/2013 | Damaser | ................ | A61B 5/205 600/561 |
| 2014/0213862 A1* | 7/2014 | Addison | ............ | A61B 5/02416 600/324 |
| 2014/0275809 A1* | 9/2014 | Schriefl | ................ | A61B 5/7246 600/300 |
| 2015/0223745 A1* | 8/2015 | Wille | ...................... | A61B 5/205 600/561 |
| 2015/0265181 A1* | 9/2015 | Flanders | ............. | A61B 5/742 600/301 |
| 2015/0297116 A1* | 10/2015 | Kilcoyne | ............... | A61B 1/041 600/302 |
| 2015/0374288 A1* | 12/2015 | Lamraoui | ............. | A61B 5/205 600/31 |
| 2016/0058355 A1* | 3/2016 | Chung | .................. | A61B 5/742 600/301 |

OTHER PUBLICATIONS

Majerus, Steve JA, et al. "Wireless, ultra-low-power implantable sensor for chronic bladder pressure monitoring." ACM Journal on Emerging Technologies in Computing Systems (JETC) 8.2 (2012): 11.

Wang, Chua-Chin, et al. "A mini-invasive long-term bladder urine pressure measurement ASIC and system." IEEE Transactions on Biomedical Circuits and Systems 2.1 (2008): 44-49.

Majerus, Steve JA, et al. "Low-power wireless micromanometer system for acute and chronic bladder-pressure monitoring." IEEE Transactions on Biomedical Engineering 58.3 (2010): 763-767.

\* cited by examiner

BLADDER EVENT DETECTION FOR DIAGNOSIS OF URINARY INCONTINENCE OR TREATMENT OF LOWER URINARY TRACT DYSFUNCTION

CROSS-REFERENCE TO RELATED APPLICATIONS

This is a Continuation patent application that claims priority to U.S. patent application Ser. No. 15/142,704, filed Apr. 29, 2016, which claims the benefit of U.S. Provisional Patent Application No. 62/154,350, filed Apr. 29, 2015, entitled SYSTEMS AND METHODS FOR CONDITIONAL BLADDER STIMULATION BASED ON AN INPUT FROM A BLADDER PRESSURE SENSOR, and U.S. Provisional Patent Application No. 62/193,238, filed Jul. 16, 2015, entitled SYSTEMS AND METHODS FOR CONDITIONAL BLADDER STIMULATION BASED ON AN INPUT FROM A BLADDER PRESSURE SENSOR. The subject matter of these applications is incorporated herein by reference in their entirety.

GOVERNMENT SUPPORT

This invention was made with government support under 1101 RX000443-01 awarded by the Rehabilitation R&D Service, Department of Veterans Affairs. The government has certain rights in the invention.

TECHNICAL FIELD

The present disclosure relates generally to the diagnosis of urinary incontinence and the treatment of lower urinary tract dysfunction and, more specifically, to systems and methods that can categorize detected bladder events, which can be used for the diagnosis of urinary incontinence or the treatment of lower urinary tract dysfunction.

BACKGROUND

Urinary incontinence is a condition affecting 200 million people worldwide that significantly reduces quality of life. Diagnosis of urinary incontinence can range from a simple clinical evaluation based on history and a physical exam to more complex tests, such as a clinical urodynamics examination, to determine if the patient has stress urinary incontinence or urgency urinary incontinence due to overactive bladder or neurogenic detrusor overactivity. Diagnosis of lower urinary tract dysfunction with urodynamics has historically relied on data acquired from two or more sensors using nonphysiologically fast cystometric filling. Extended ambulatory urodynamics testing can provide more data collected at physiologically normal fill rates. However, this two-sensor system provides an inconvenient and uncomfortable solution for extended ambulatory urodynamics testing. An alternative method of measuring bladder activity over extended durations at natural fill rates would improve diagnosis of urinary incontinence.

For treatment of urinary dysfunctions, electrical stimulation has been shown to effectively inhibit unwanted bladder contractions in both spinal cord injury patients and neurally intact patients. Currently, state-of-the-art electrical stimulation has focused on open-loop neuromodulation. However, this open-loop stimulation is not ideal because the neural pathways could become habituated to continuous stimulation of sensory nerves, potentially reducing the effectiveness of stimulation over time. Stimulation settings may need to be adjusted over time, typically by the clinician. In addition, individuals with neurogenic detrusor overactivity require feedback of bladder activity in the absence of sensation to determine when to empty their bladders, and those with sensation may not wish for stimulation to be continually active. Accordingly, closed-loop control would improve such neuromodulation, but the closed-loop control requires feedback to determine bladder activity.

SUMMARY

The present disclosure relates generally to the diagnosis of urinary incontinence or the treatment of lower urinary tract dysfunction and, more specifically, to systems and methods that can categorize detected bladder events, which can be used for the diagnosis of urinary incontinence or the treatment of lower urinary tract dysfunction. The systems and methods can categorize bladder events detected by a single sensor (e.g., a bladder pressure sensor) in real time. For example, the bladder events can be categorized into three types: bladder contraction resulting in voluntary voiding, bladder contraction without voluntary voiding, and a non-contraction event that would change bladder pressure, such as a cough. The diagnosis and treatment can be facilitated based on the automated categorization of the bladder events.

In one aspect, the present disclosure includes a system that can categorize detected bladder events. The system can include a sensing device that can include a pressure sensor to directly detect a pressure within the bladder. The sensing device can be adapted to be located within the bladder. The system can also include a signal processing device to: receive a signal indicating the detected pressure within the bladder; detect a bladder event based the detected pressure within the signal; and characterize the bladder event as a contraction event or a non-contraction event.

In another aspect, the present disclosure includes a method for categorizing detected bladder events. The method can be performed by a signal processing device comprising a processor. The method can include receiving a signal indicating a pressure detected within the bladder from a sensing device, comprising a pressure sensor, located within the bladder. The method can also include detecting a bladder event based on the detected pressure within the signal. The method can also include characterizing the bladder event as a contraction event or a non-contraction event.

In a further aspect, the present disclosure includes a sensor device implantable within a bladder wall. The sensor device includes at least a pressure sensor to detect a pressure within the bladder, a battery that is rechargeable by a radio frequency (RF) signal, and an inductive antenna to receive the RF signal for recharging and to transmit a signal comprising the detected pressure. The sensor device can be configured to transmit the signal to a signal processing device to detect and categorize one or more bladder events within the signal.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
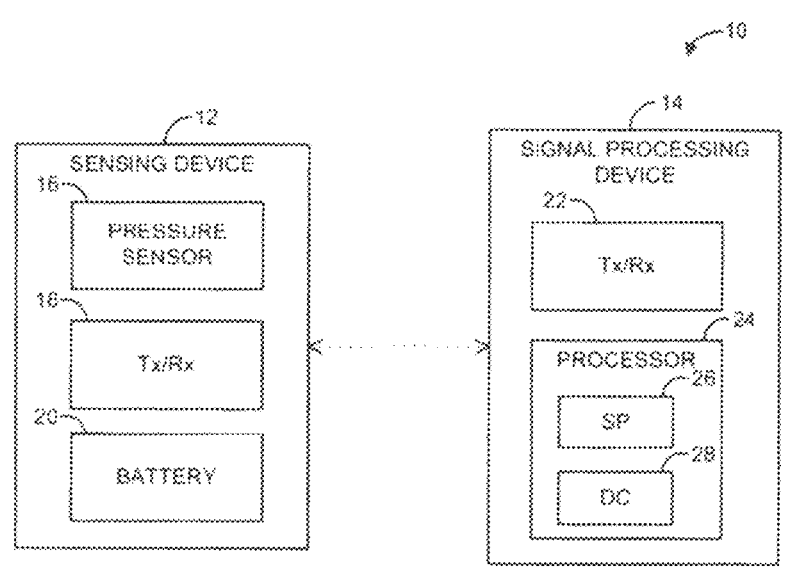
FIG. 1 is a block diagram showing a system that can categorize detected bladder events in accordance with an aspect of the present disclosure.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/ steps) is not limited to the order presented in the claims or figures unless specifically indicated otherwise.

As used herein, the term "sensing device" can refer to a device that can detect a property of a subject's bladder. In some instances, at least a portion of the sensing device can be implanted within a wall of the subject's bladder to detect the property of the subject's bladder. The sensing device can include a sensor specific to the property that is detected. In some examples, the sensing device can include an implantable pressure sensor, such as a bridge-type circuit, to detect a pressure within the bladder. In this example, the sensing device can also include additional components, such as a transmitter, a battery, a drift cancellation circuit, or the like. The sensing device including the pressure sensor can be implanted within a wall of the patient's bladder. In another example, the sensing device can include an implantable pressure sensor and another external sensor (e.g., an accelerometer, such as a three-axis accelerometer). While the pressure sensor can be implanted within the wall of the bladder, the external sensor can be located external to the subject's body.

As used herein, the term "signal processing device" can refer to a device that includes at least a processor to perform signal processing on a signal including the detected pressure and detect a bladder event based on the processed signal. For example, the signal processing device can be a real-time computing platform, such as an application specific integrated circuit (ASIC), an embedded circuit running software, custom programmable hardware, or software on a conventional computing platform, such as a personal computer, a tablet computer, a smartphone, or the like. In some instances, the signal processing device can be implantable. In other instances, the signal processing device can be external. In still other instances, the signal processing device can be at least partially implanted and at least partially external.

As used herein, the term "bladder event" can refer to a detectable change in the bladder pressure. The detected bladder event can be characterized as a contraction event or a non-contraction event. For example, the contraction event can be further classified as a voiding contraction event (e.g., due to a neural signal) or a non-voiding contraction event (e.g., due to a non-neural event, like coughing, laughing, change in posture, or the like). In some instances, the non-contraction event can include an artifact.

As used herein, the term "voiding contraction" can refer to a contraction of the detrusor muscle of the bladder, which generates an urge to urinate. In some instances, if not stopped, the bladder contraction can force urine out of the bladder and/or cause pain.

As used herein, the term "signal processing" can refer to one or more techniques that can improve the accuracy and reliability of an input signal (e.g., the signal from the pressure sensor). For example, the signal processing can include one or more techniques often applied to biomedical signals to condition the signal, including digital filtering, multi-level wavelet approximations, and the like.

As used herein, the term "thresholding procedure" can refer to a multi-resolution, context-aware wavelet analysis procedure that efficiently considers local and global trends in the signal. In some instances, the thresholding procedure can include a set of tunable parameters. In other instances, the thresholding procedure can include pattern matching.

As used herein, the term "tunable parameter" can refer to an adjustable variable that has a documented effect on behavior that can be adjusted for a specific patient. In some instances, the tunable parameter can be part of a set of tunable parameters.

As used herein, the term "neuromodulation device" can refer to a device that can stimulate one or more nerves to control over-active bladder and/or incontinence. In some instances, the stimulation can be an electrical stimulation. For example, the stimulation can be "conditional" so that the stimulation occurs based upon detection of a bladder contraction.

As used herein, the term "subject" can refer to any warm-blooded organism including, but not limited to, a human being, a pig, a rat, a mouse, a dog, a cat, a goat, a sheep, a horse, a monkey, an ape, a rabbit, a cow, etc. The terms "patient" and "subject" can be used interchangeably herein.

II. Overview

The present disclosure relates generally to the diagnosis of urinary incontinence and the treatment of lower urinary tract dysfunction and, more specifically, to systems and methods that can categorize detected bladder events, which can be used for the diagnosis of urinary incontinence or the treatment of lower urinary tract dysfunction. For example, the detected bladder events can be classified into different categories, including contraction event and non-contraction event. The systems and methods described herein require only a single sensor (e.g., a pressure sensor implanted into the bladder wall) to record the signal that is used to detect and categorize the bladder events. This single sensor is less invasive than traditional solutions that generally rely on two pressure sensors and/or two catheters to record bladder events, making the previous solutions uncomfortable, impractical, and, often, non-physiological.

The systems and methods described herein can accomplish the categorization of the bladder events with a high degree of accuracy and a low false positive rate. The systems and methods described herein utilize signal processing techniques often applied to biomedical signals to detect and categorize the bladder events from the signal recorded by the single sensor. For example, digital filtering and multi-level wavelet approximations can be used to condition the input before applying a multi-resolution context-aware thresholding technique that efficiently considers local and global trends in the signal to facilitate categorizing the bladder events. The context-aware thresholding technique can utilize one or more tunable parameters that can be tuned to the individual subject to achieve an optimal result for the individual subject.

III. Systems

One aspect of the present disclosure can include a system 10 (FIG. 1) that can categorize detected bladder events, which can be used for the diagnosis of urinary incontinence or the treatment of lower urinary tract dysfunction. The system 10 can include a single sensing device 12 that can detect a property of the bladder (e.g., a pressure within the bladder) and transmit a signal that includes the detected property and a signal processing device 14, which can detect and categorize the detected bladder events from the signal. For example, the bladder events can be categorized as a contraction event (which can be further classified as a voiding event or a non-voiding event) or a non-contraction event. Notably, the system 10 does not require a second sensing device and can categorize the detected bladder events from a single sensing device 12.

The sensing device 12 can be an in vivo sensor that can be implanted within body tissue or a fluid-filled cavity. In some instances, the sensing device 12 can be implantable within a subject's bladder. For example, the sensing device 12 can be implantable within a wall of the bladder where lumen pressure is transduced. Accordingly, the sensing device 12 can be made of a biocompatible material, coated with a biocompatible material, and/or housed within a biocompatible material. The sensing device 12 can be delivered, in some instances, into the bladder by a cytoscope. Accordingly, the sensing device 12 can be at least partially hermetically sealed and sized and dimensioned to facilitate the delivery by a 24-French cytoscope (e.g., measuring no larger than 3.5×7×15 mm). The sensing device 12 can also be sized and dimensioned to erosion and migration through the bladder muscle.

The sensing device 12 can include at least a pressure sensor 16, a wireless transceiver 18, and a rechargeable battery 20. The pressure sensor 16 can include at least a bridge-type configuration to detect changes in the pressure of the bladder. For example, the pressure sensor 16 can be implemented by electrical resistors, piezoresistive components, resistors implemented on a MEMS device, or the like. The pressure sensor 16 can be included in a circuit with components accounting for offset or drift cancellation. The wireless transceiver 18 can send a signal including the detected pressure to the signal processing device 14. The rechargeable battery 20 can provide power to the pressure sensor 16, the wireless transceiver 18, and/or additional components of the sensing device 12. In some instances, the rechargeable battery 20 can provide power without being recharged for at least 12 hours. In other instances, the rechargeable battery 20 can provide power without being recharged for at least 24 hours. In still other instances, the rechargeable battery 20 can provide power without being recharged for at least 48 hours. For example, the rechargeable battery 20 can be recharged based on a received radio frequency (RF) signal. The wireless transceiver 18 can receive the RF signal and facilitate recharging the rechargeable battery 20.

The sensing device 12 can send a signal reflective of the detected pressure to the signal processing device 14. The signal processing device 14 can include a transceiver 22 (that includes at least a receiver) to receive the transmitted signal. The signal processing device 14 also includes a processor 24 that can process the transmitted signal to accomplish the characterization of the bladder events. For example, a signal processing unit (SP) 26 of the signal processing device 14 can utilize signal processing techniques often applied to biomedical signals to condition the signal from the sensing device 12. The signal processing techniques can remove noise (e.g., background electrical noise, biological noise, and the like) from the biological signal. For example, the signal processing techniques can include digital filtering, multi-level wavelet approximations, etc. The signals are conditioned by the signal processing techniques before a characterization unit (DC) 28 of the signal processing device 14 applies a multi-resolution context-aware thresholding technique to the signal. The multi-resolution context-aware thresholding technique can be used to characterize a detected bladder event as a contraction event (which can be further characterized as a voiding contraction or a non-voiding contraction) or a non-contraction event.

For example, the multi-resolution context-aware thresholding technique can efficiently consider local and/or global trends in the signal prior to making a decision whether or not to stimulate. The multi-resolution context-aware thresholding technique can be customized for an individual patient. The multi-resolution context-aware thresholding technique can depend on one or more tunable parameters that can be tuned for the individual patient, achieving the highest level of accuracy possible for the patient. The tunable parameters can each exhibit a documented effect on behavior of the signal processing device 14 with regard to when it recommends stimulating the bladder. The tunable parameters can be adjusted and stored in the memory of the signal processing device 14. For example, the tunable parameters can be adjusted and sent via a wireless signal to the signal processing device 14. Examples of the tunable parameters can include a window size, a sensitivity, or the like.

Figure 2:
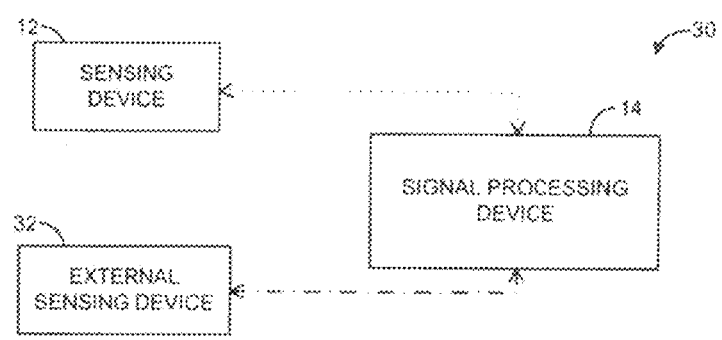
FIG. 2 is a block diagram showing an external sensing device that can be employed by the system in FIG. 1.

Referring now to FIG. 2, illustrated is an example of a system 30 that can include an external sensing device 32 to aid in the event detection by the signal processing device 14. The external sensing device 32 can be located on or near the abdomen of the subject. The external sensing device 32, in some instances, can include a three-axis accelerometer to detect external motion (e.g., of the abdomen). The signal from the sensing device 12 can be correlated to a signal from the external sensing device 32 by the signal processing device 14. Based on the correlated signal, the signal processing device 14 can characterize a detected bladder event as a contraction event or a non-contraction event. For example, the signal from the external sensing device 32 can indicate movement of the abdomen during a non-contraction event, but no movement of the abdomen during a contraction event. The signal processing device 14 can reject the non-contraction event from further processing.

Figure 3:
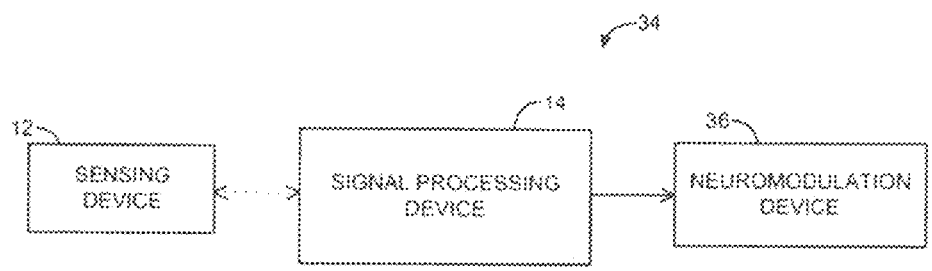
FIG. 3 is a block diagram showing an example neuromodulation device that can be signaled by the system in FIG. 1.

FIG. 3 shows a conditional stimulation system 34, which is an example application that can use the categorized bladder events. The conditional stimulation system 34 includes a single sensing device 12 (e.g., a pressure sensor located within a subject's bladder) and a signal processing device 14. The signal processing device 14 can signal a neuromodulation device 36 (e.g., including an electrical stimulator, a magnetic stimulator, or the like) to deliver a stimulation. The stimulation can be used to prevent voiding and/or to prevent leakage depending on the event characterization. In some instances, the signal processing device 14 can also configure one or more parameters of the stimulation based on the detected pressure so that the stimulation is patient-specific.

The signal processing device 14 can send a signal to the stimulator of the neuromodulation device 36 indicating a need for stimulation (e.g., based on one or more results of the multi-resolution context-aware thresholding procedure). The signal, in some examples, can also include one or more parameters for the stimulation. In some instances, the signal sent from the signal processing device 14 to the stimulator of the neuromodulation device 36 can be a digital signal. For example, the digital signal can be transmitted wirelessly, sent through a wireless transmitter of the signal processing device 14 to a wireless receiver of the stimulator of the neuromodulation device 36. The stimulator of the neuromodulation device 36 can provide an electrical signal for bladder stimulation based on a signal from the signal processing device 14 indicating that a condition has occurred in the bladder that necessitates the stimulation.

IV. Methods

Figure 4:
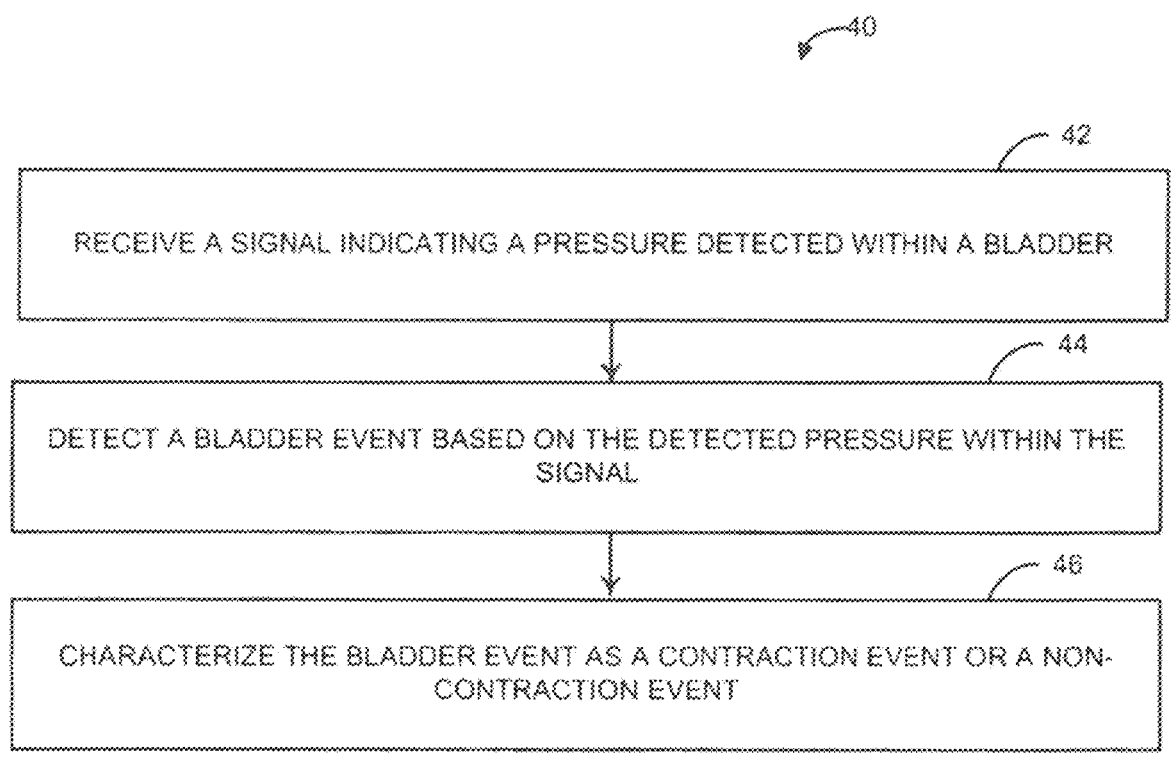
FIG. 4 is a process flow diagram illustrating a method for categorizing detected bladder events according to another aspect of the present disclosure.
Figure 5:
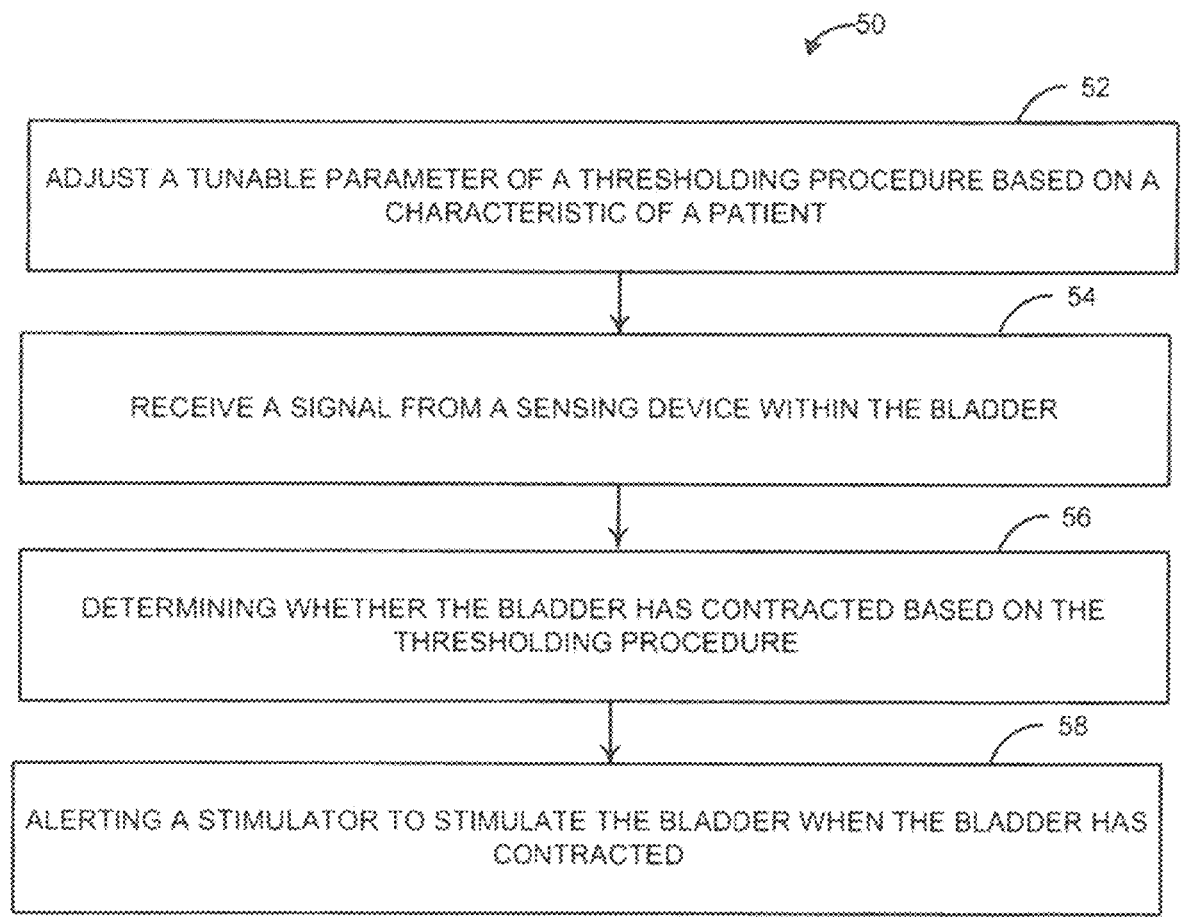
FIG. 5 is a process flow diagram illustrating a method for individualized conditional bladder stimulation according to yet another aspect of the present disclosure.

Another aspect of the present disclosure can include methods that can be used for the diagnosis of urinary incontinence or the treatment of lower urinary tract dysfunction. One example of a method 40 for categorizing detected bladder events for the diagnosis of urinary incontinence or the treatment of lower urinary tract dysfunction is shown in FIG. 4. Another example of a method 50 for individualized conditional bladder stimulation is shown in FIG. 5.

The methods 40 and 50 are illustrated as process flow diagrams with flowchart illustrations, which can be implemented by an ASIC and/or by a general purpose computer processor. For purposes of simplicity, the methods 40 and 50 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 40 and 50.

FIG. 4 illustrates a method 40 for categorizing detected bladder events. The categorized bladder events can be utilized for the diagnosis of urinary incontinence or the treatment of lower urinary tract dysfunction. The method 40 can be performed, for example, by the system 10 shown in FIG. 1.

At 42, a signal can be received (e.g., by a signal processing device 14) indicating a pressure detected within a bladder (e.g., from a sensing device 12 including a pressure sensor 16). For example, the sensing device can be implanted within a wall of the bladder. The pressure sensor can detect changes in the pressure corresponding to various bladder events (e.g., contraction events or non-contraction events). These changes can be included in the signal.

The signal can be wirelessly transmitted from the sensing device and received by the signal processing device. In some instances, the signal processing device can perform one or more pre-processing techniques on the signal before bladder events are detected. The pre-processing techniques can include those techniques that are often applied to biomedical signals to condition the biomedical signals for further processing. One example pre-processing technique can include filtering the signal (e.g., via a digital low pass filter). For example, the low pass filtering can include a exponential moving average with a certain low pass cutoff frequency.

At 44, a bladder event can be detected (e.g., by a signal processing device 14) based on the detected pressure within the signal. The signal can undergo a multi-level discrete wavelet decomposition procedure. The multi-level wavelet decomposition can extract frequencies of interest corresponding to the bladder event. The wavelets can be constructed to minimize the number of filter coefficients required to approximate a given signal, reducing the computational burden of the method 40.

At 46, the bladder event can be characterized (e.g., by a signal processing device 14) as a contraction event or a non-contraction event. The characterization can be based on an adaptive thresholding and classification procedure. For example, the adaptive thresholding can include a multi-resolution context-aware thresholding technique that efficiently considers local and global trends in the signal to facilitate the classification. The thresholding procedure can be customized for an individual patient, depending on one or more tunable parameters to achieve the highest level of accuracy possible for the patient. For example, the tunable parameters can be adjusted and sent via a wireless signal to the signal processing device.

The output of the method 40 can include the classified events (e.g., either contraction events—which can be further classified as voiding contractions or non-voiding contractions—or non-contraction events). The output can be used in the diagnosis of urinary incontinence or the treatment of lower urinary tract dysfunction.

For example, the treatment of lower urinary tract dysfunction can include conditional bladder stimulation to block voiding or to prevent leakage when the bladder event is characterized as the contraction event. In some instances, one or more parameters of the stimulation can be configured based on the detected pressure.

FIG. 5 shows a method 50 for individualized conditional bladder stimulation. The method 50 can be executed, for example, by the system 34 of FIG. 3. At 52, one or more tunable parameters of a thresholding procedure can be adjusted based on one or more characteristics of the patient. Adjusting the tunable parameters for the patient creates a bladder stimulation mechanism that is geared to the patient rather than geared for a population of patients. Accordingly, the thresholding procedure can be adapted to different patients through the configuration of multiple tuning parameters.

At 54, a signal from a sensing device within the patient's bladder can be received. The sensing device can include a pressure sensor. In some instances, the sensing device can also include a three-axis accelerometer, which can be used to reject pressure signals associated with one or more artifacts (e.g., a motion artifact). This can facilitate the detection of bladder contractions without the need for an abdominal pressure sensor. At 56, based on the thresholding procedure, it can be determined whether the bladder has contracted. This determination can be used to decide whether to stimulate the bladder. At 58, a stimulator can be alerted to stimulate the bladder when the bladder has contracted. For example, the alert can be a digital signal triggered by a result of the thresholding procedure.

V. Experimental

The following experiment shows a real-time, highly accurate bladder event detection system that does not require a reference sensor.

Methods

Vesical Pressure Signal Processing

Figure 6:
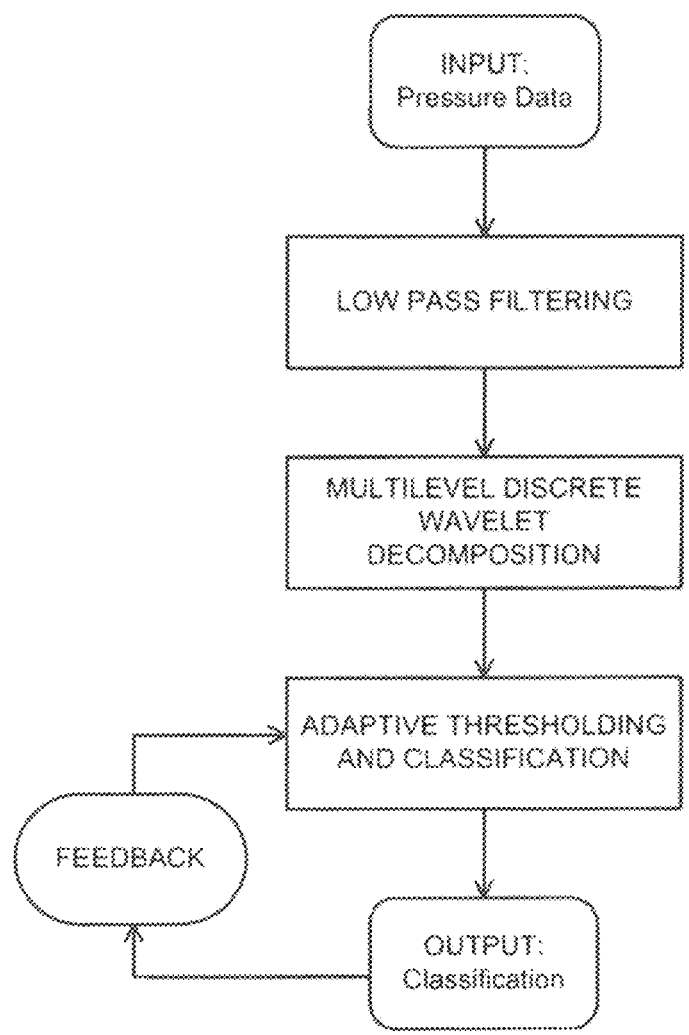
FIG. 6 is a diagrammatic showing of an algorithm for categorizing detected bladder events.

The basic algorithm structure includes three stages: initial filtering, wavelet transform, and adaptive thresholding (FIG. 6). The signal is initially filtered using an exponential moving average (EMA), with a low pass cutoff frequency of 0.01 Hz. EMA filtering is chosen because it allows the system to operate in an almost predictive manner by assuming that repeated spikes in pressure can potentially result in a true bladder contraction. For a hardware implementation, the computation is inexpensive, requiring very few operations and a single unit of delay, enabling real-time operation. Furthermore, by filtering close to DC, changes in pressure are effectively limited to those caused by passive stretching of the bladder. Contractions, which occur at higher frequencies, are sustained, and while slightly attenuated, remain present in the output. The output of the EMA is then processed by applying a multilevel discrete wavelet transform. The Daubechies 4 wavelet was chosen as the basis function for use in the algorithm. This wavelet was chosen for its performance at extracting frequencies of interest for this application and its ease of implementation. Furthermore, the wavelets are constructed to minimize the number of filter coefficients required to approximate a given signal, reducing the computational burden on hardware implementation.

In clinical urodynamics, the effects of artifacts are negligible as patient motion and activity level are controlled, and a global threshold can work well for detecting bladder contractions. However, for ambulatory urodynamics without an abdominal reference sensor, a fixed threshold is vulnerable to patient movement and sensor drift. Thus, an adaptive threshold, which considers local trends in the data, may be more robust in a real-world, ambulatory setting. Two statistical methods of adaptive thresholding were investigated, which consider either the mean and standard deviation or the quantiles within a given window size.

Using standard-deviation-based thresholding, the algorithm labels a contraction when the approximation of the vesical pressure rises two standard deviations above the window mean. Similarly, artifacts are considered to occur when the detail coefficients, or outputs from the high pass filters, rise by the same amount. At this stage the original signal is heavily processed. Therefore, any residual artifacts will cause spikes in the detail coefficients, enabling detection. Since the bladder pressure approximation does not change significantly between subsequent windows, the mean need not be recomputed for each sample, providing a trade off between power savings and accuracy in hardware implementation.

Using the quantile-based adaptive thresholding, the values in the window are sorted by rank order. Samples in either the approximation or detail coefficients exceeding a threshold percentile are considered bladder events or artifacts, where the threshold percentile may be adjusted by the physician. Since the list remains partially sorted, new samples can be rapidly inserted into the list. Furthermore, separate significance threshold values for approximation and detail coefficients allow algorithm tuning based on the desired detection and false positive rates.

Algorithm Optimization and Output

The ability to optimize algorithm performance for a specific user is crucial to the successful implementation of the framework. To enable user-specific optimization, we introduced a set of tunable input parameters into the system. To provide this level of flexibility, the tunable parameters included (1) sample buffer length, (2) approximation coefficient sensitivity, and (3) detail coefficient sensitivity. The sample buffer length refers to the time in seconds of history to retain, while the approximation and detail coefficient sensitivity refer to the percentile required for a new input value to be classified as the start of a contraction or artifact, for approximation and detail coefficients, respectively. A high value for the sample buffer length could result in a prohibitively large history buffer. At each level of the discrete wavelet transform, however, the data rate is halved, so it is possible to store a longer history with fewer samples while retaining the general trend of the signal. Furthermore, in a hardware implementation, this reduces the area overhead, delay, and power consumption for computing the local threshold. The second and third parameters affect the probability that the algorithm will attribute pressure increases to actual bladder contractions or artifacts, and they can be individually adjusted to achieve the desired performance.

Three quantifiable metrics were defined from the output of the algorithm: (1) the success or failure of event detection (X), effectively the true positive rate; (2) the number of false positives detected per contraction event (Y), and the duty cycle of the stimulator, which measures the time the stimulator is on divided by the total duration of the recording (Z). Together, these metrics aggregate the effectiveness of the algorithm at detecting an unwanted bladder event with sufficiently short delay to prevent the unwanted event with electrical stimulation. A cost function was defined, termed the Conditional Stimulation Score (CS Score), which combines these three metrics to tune the algorithm and to compare performance to other algorithms:

$$CS\_Score(x, y, z) = x^2 - \left(\frac{y}{100} + \frac{|z|}{10}\right)$$

$$x = \frac{EventsDetected}{TotalEvents}$$

$$y = \frac{FalsePostives}{1 + EventsDetected}$$

$$z = \frac{DCactual - DCideal}{DCideal}$$

$$DCactual = \frac{Tstim}{Ttotal}, DCideal = \frac{Tcontraction}{Ttotal}$$

Due to the importance of a high detection rate, the percentage of true positives (x) is squared in order to penalize input parameters resulting in a value below 1, while perfect detection remains unchanged. False positives (y) and duty cycle deviation (z) are linear terms weighted such that every 5 false positives and every ±50% deviation from the ideal duty cycle result in an equivalent decrease in CS Score. Additionally, combining these terms allows the system to compensate for either (1) a high number of short duration false positives (i.e. high y, low z), or (2) a small number of high duration false positives (i.e. low y, high z), which result in scoring penalties regardless.

Figure 7A:
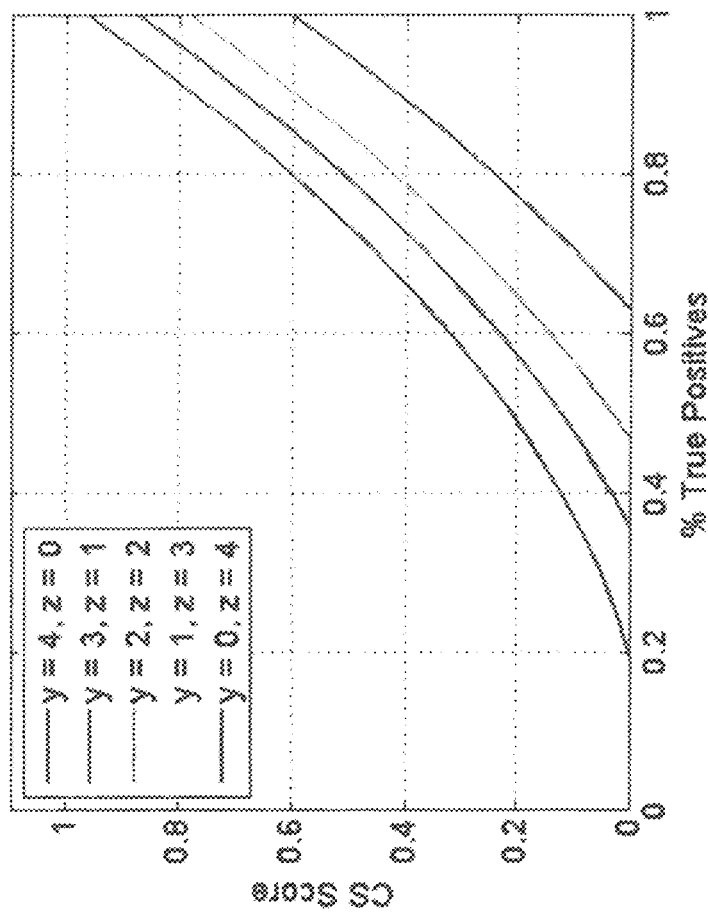
FIGS. 7A-FIG. 7C shows plots of example Conditional Stimulation (CS) Scores for various parameter combinations.
Figure 7B:
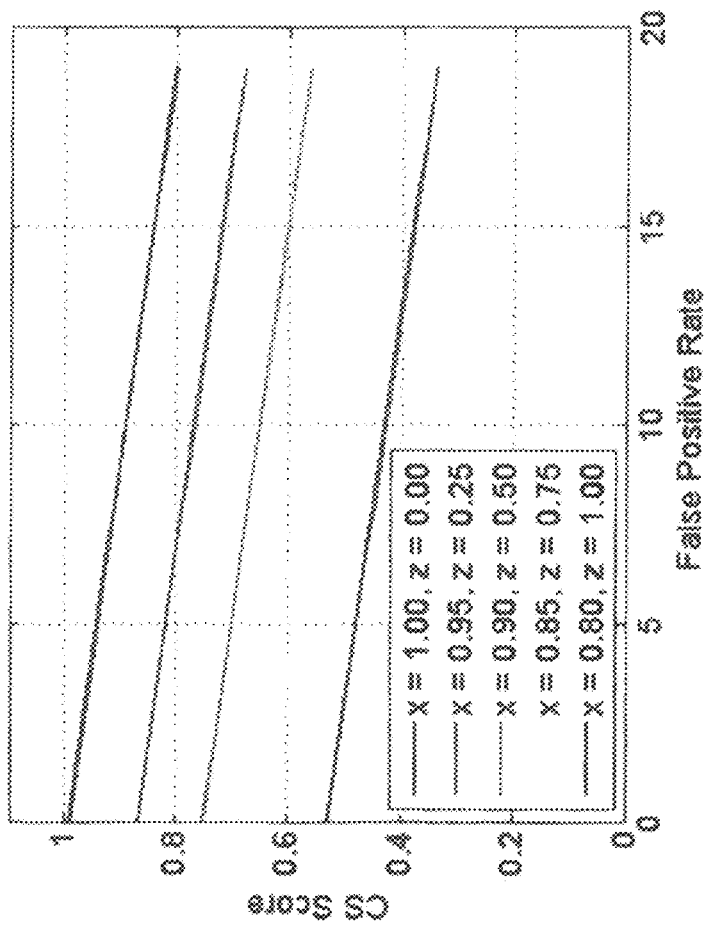
Figure 7C:
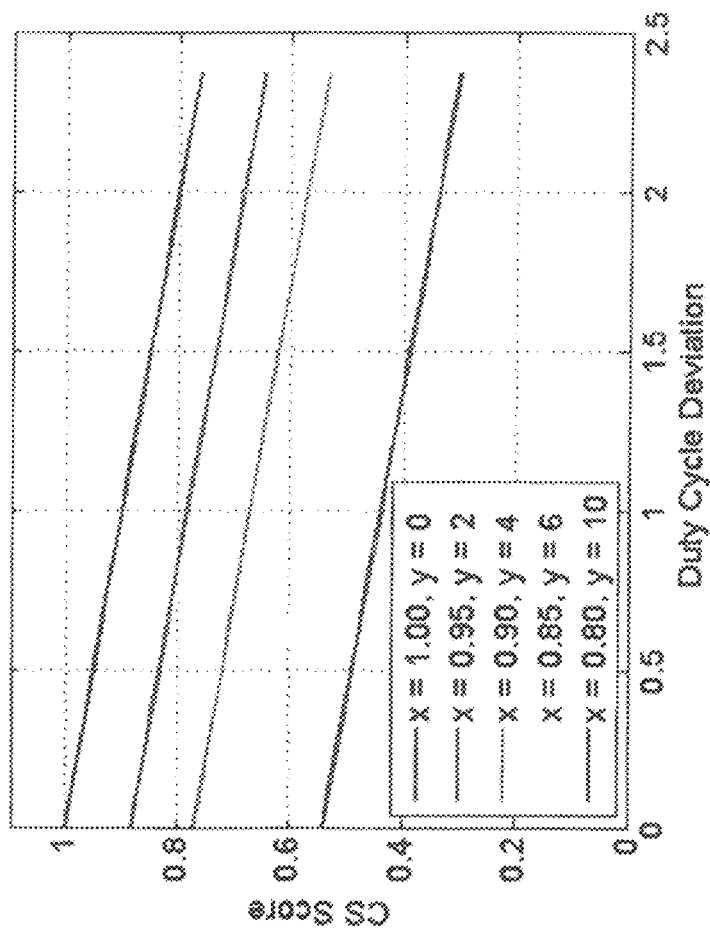

Example CS Scores for various parameter combinations are shown in FIG. 7. Algorithms may have the potential for a significant number of false positives, especially with noisy or real-world data, and so values ranging from 0 to 20 have been chosen to demonstrate the effect that a high number of false positives will have on the algorithm score.

Human Data Acquisition

Urodynamic examinations providing vesical and abdominal pressure data were collected from a total of 64 tracings from 14 human subjects sampled at 100 Hz. Note that these data were not collected for the purpose of developing this algorithm, and the sampling rate was chosen or set by the clinical equipment for the particular needs. Subjects had neurogenic detrusor overactivity and 2-9 cystometric fills were completed. These clinical tests were conducted at the Louis Stokes Cleveland Department of Veterans Affairs in Cleveland, Ohio (IRB #12023-H12). All procedures followed protocols that were reviewed and approved by the Institutional Review Board and followed standard clinical practices.

Pressures were recorded as part of clinically standard urodynamics test, which involves filling the bladder with saline to observe its behavior. Briefly, a dual lumen intraurethral catheter was inserted, with one lumen used to infuse saline into the bladder at approximately 50 ml/min, depending on the clinical scenario, and the other lumen used to measure continuous vesical pressure via an external fluidic transducer. In addition, an anorectal balloon catheter was inserted to similarly measure continuous abdominal pressure; continuous detrusor pressure was calculated as the difference between the vesical and rectal pressures. Filling was continued until a reflex bladder contraction was evoked, which usually resulted in voiding around the urethral catheter. After each cystometric fill the bladder was completely emptied.

Algorithm Evaluation

To evaluate the efficacy of the CAT algorithm classifying bladder contractions, and to compare to other methods, the algorithms were implemented in Matlab (Mathworks, Natick, Mass.) and tested with the recorded urodynamics data from human subjects. A summary of the algorithms tested is provided in Table I.

Three other methods besides those from literature (SDT and HDT), and the proposed method (CAT), are also included for comparison purposes. Global Detrusor Thresholding (GDT) and Global Vesical Thresholding (GVT), which are derived from SDT, are used to demonstrate how a static thresholding method may be viable on either detrusor (GDT) or vesical (GVT) pressures if the threshold is tuned to an individual. Adaptive Vesical Thresholding (AVT), which is a variant of CAT, does not include an intermediate Discrete Wavelet Transform (DWT), and is used to demonstrate the effect of performing thresholding on the wavelet coefficients rather than the time domain signal.

During testing, a real-time environment was simulated in which the algorithms were limited to accessing data on the time course in which it was produced, without access to future data. Then, for each algorithm, the CS Score was calculated to compare their performances. Algorithms were tuned using two methods. Firstly, they were tuned to each individual using only the first of the available urodynamics tracings; parameters generated from each training set were applied to the same individual. Secondly, algorithms were tuned to a subset of 14 tracings, one from each patient, and applied to the entire dataset.

For both training methods, the onset of a contraction was identified by inspection. Each recorded cystometric fill contained exactly one voiding contraction, thus any events detected outside of this range were considered to be false positives. To effectively inhibit an unwanted contraction, stimulation must occur well before the leak point pressure is reached; therefore, it was assumed that contractions must be detected within 1 second for effective stimulation, and any events detected after this time were considered missed events.

Algorithm Tuning

While SDT and HDT were implemented as described in the literature, the other methods were tuned to individuals by modifying parameters to maximize the CS Score for that algorithm. These parameters include the low pass filter cutoff frequency (for all tuned algorithms), as well as algorithm-specific parameters: static threshold (GDT and GVT), history buffer length (AVT and CAT), sensitivity (AVT), and approximation/detail sensitivities (CAT). Thresholds between −50 and 50 cmH20 were tested for GDT and GVT. Windows ranging from 5 to 120 second< > were tested for both AVT and CAT Sensitivities between 0 and 1 were tested for AVT sensitivity, and both approximation and detail coefficients for CAT. These parameters were found to have a significant impact on the performance of each algorithm, with per-subject detection accuracies ranging from 0 to 100%, false positive rates ranging from none to hundreds, and CS Scores ranging from negative tens to nearly perfect scores. The algorithm was considered tuned when a parameter combination resulting in the largest CS Score was found. Similarly, a global tuning method was explored,

TABLE I

Summary of the Six Algorithms Tested

| Type | Name | Abb. | Tuned? | Inputs | Description |
|---|---|---|---|---|---|
| Static | Static Detrusor Thresholding | SDT | No | 0 | Static Threshold on $P_{det}$ |
| | Global Detrusor Thresholding | GDT | Yes | 1 | Static Threshold on $P_{det}$ |
| | Global Vesical Thresholding | GVT | Yes | 1 | Static Threshold on $P_{ves}$ |
| Hybrid | Hybrid Detrusor Thresholding | HDT | No | 0 | Moving average + static threshold on $P_{det}$ |
| Adaptive | Adaptive Vesical Thresholding | AVT | Yes | 2 | Moving threshold on $P_{ves}$ |
| | Context Aware Thresholding | CAT | Yes | 3 | Moving threshold on approximation of $P_{ves}$ | where parameters were tuned based on a subset of the data and applied to the remainder. Here, a more robust algorithm would still perform well, though not as well as with individualized tuning.

In practice, the sudden and repeated application of conditional stimulation could cause patient discomfort, so parameter optimization must seek to (1) maximize detection accuracy, (2) minimize false positives, (3) minimize detection latency between contraction onset and event detection, and (4) minimize the stimulator duty cycle. Failure to select appropriate parameters can result in oversensitivity to noise or other low amplitude pressure fluctuations. With optimally chosen parameters, a reliable and robust algorithm will have consistently high detection rates while similarly limiting the number of false positives.

Resulting CS Scores were analyzed using Tukey's pairwise comparison (p<0.05) to determine if CAT is more effective than the other methods for detecting bladder contractions. Data from tuned methods and untuned methods were pooled to determine if tuning can improve efficacy. Finally, data from static methods (GDT, GVT) and adaptive methods (AVT, CAT) were pooled and tested to determine if adaptive methods are more effective than the static methods.

Results

Context Aware Thresholding (CAT)

Figure 8:
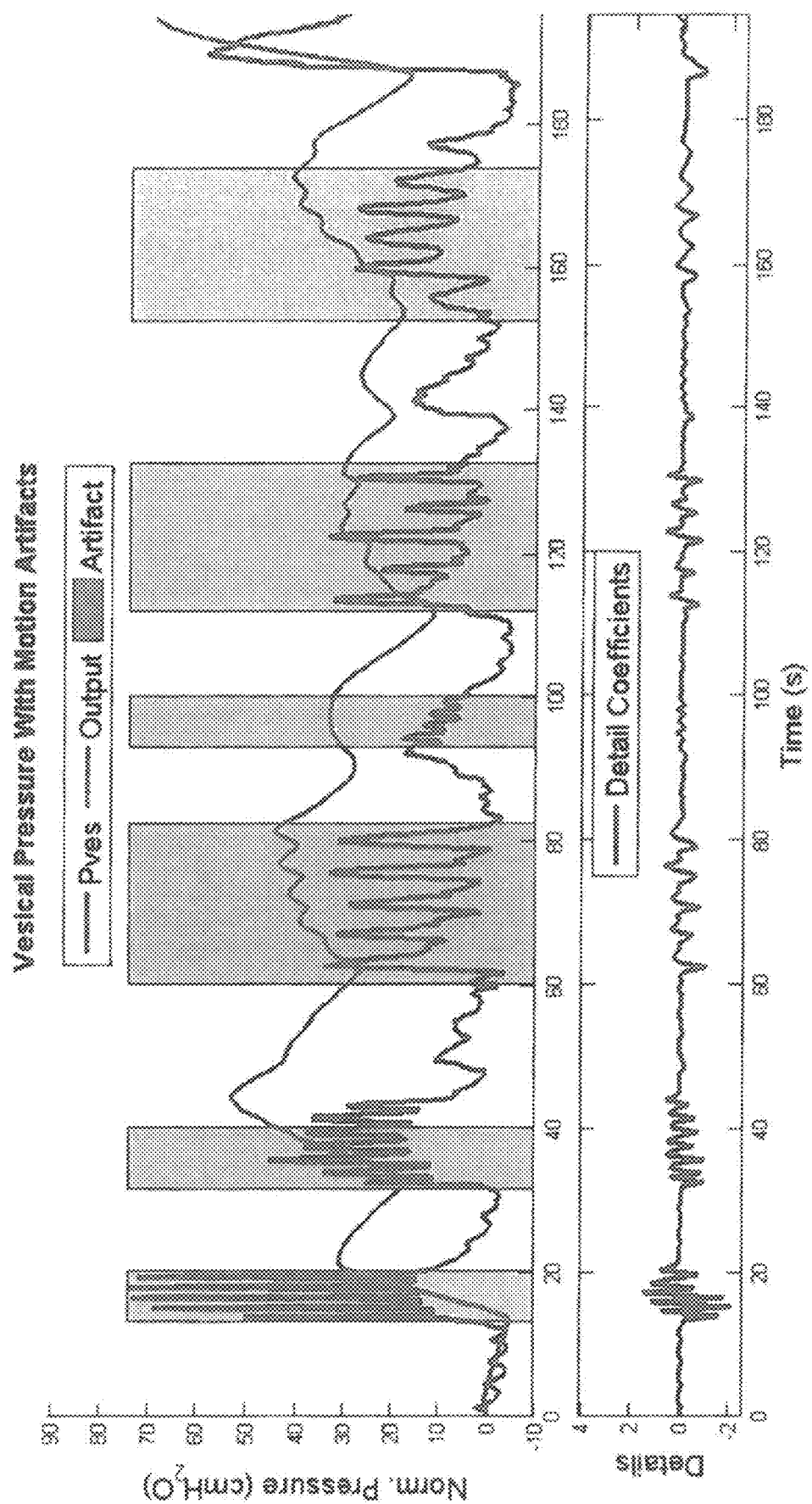
FIG. 8 shows plots that facilitate the detection of artifacts due to abdominal pressure changes.

Bladder pressure is a smooth signal relative to pressures caused by abdominal pressures, and slopes in an appropriately sized window can be approximated well with linear functions. Most artifacts due to abdominal pressure changes, such as those initiated by coughs, laughs, and sneezes, generally present as abrupt, transient spikes in the vesical pressure, and thus appear in the detail coefficients, as shown in FIG. 8, where they were analyzed as potential artifacts. While simple changes in posture could have an effect on the vesical pressure, these types of slowly changing pressure artifacts were not tested in this study because they were not reliably present in the data set.

Figure 9A:
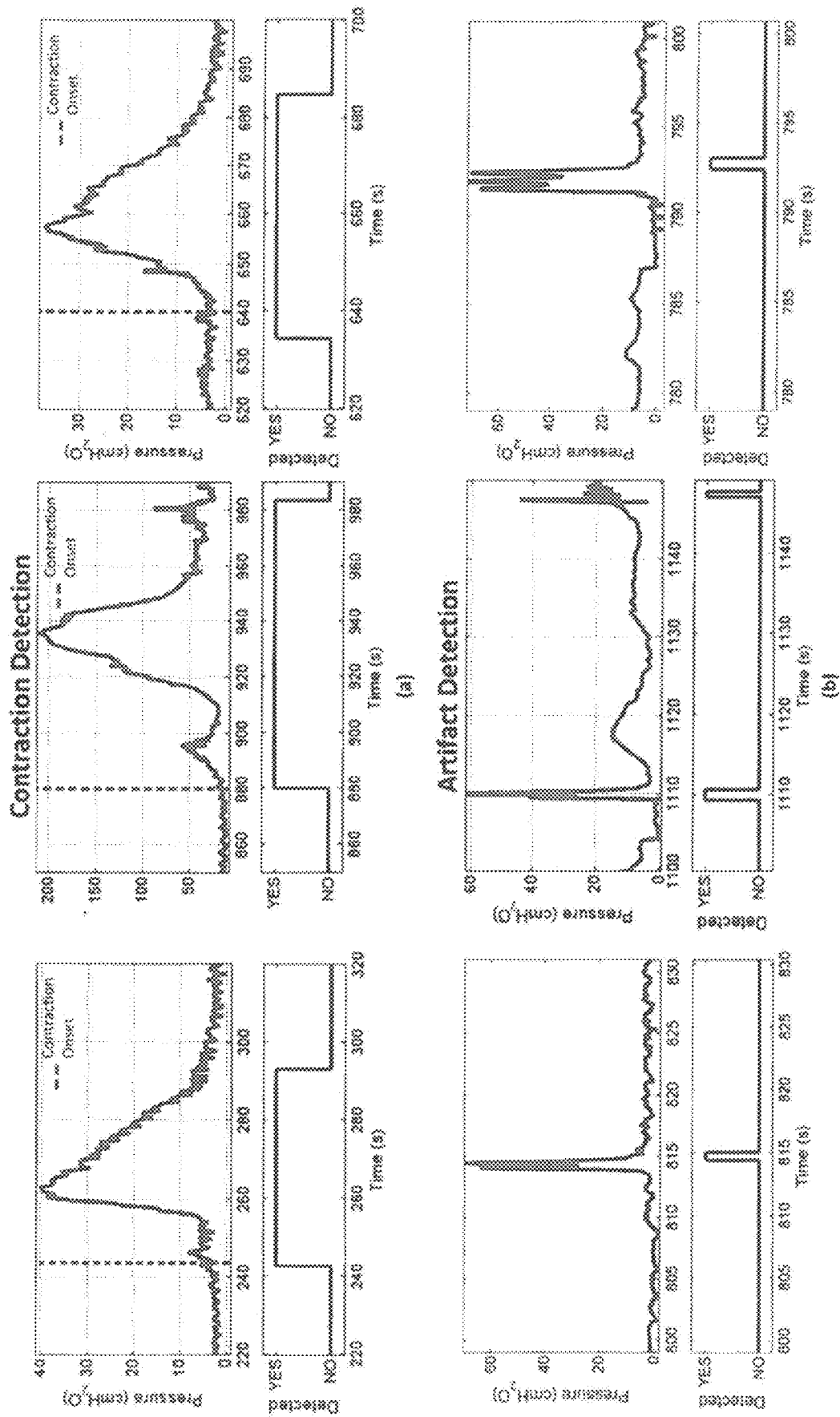
FIG. 9A and FIG. 9B show plots of sample outputs of the algorithm shown in FIG. 6.
Figure 9B:
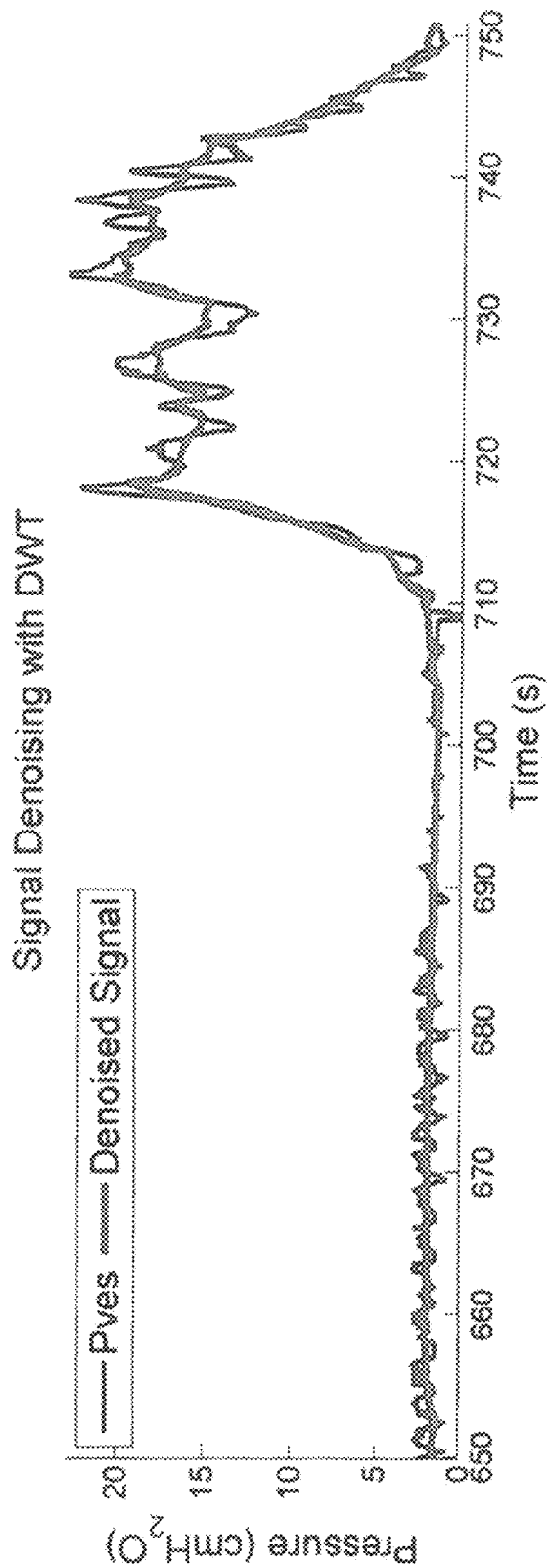
Figure 10A:
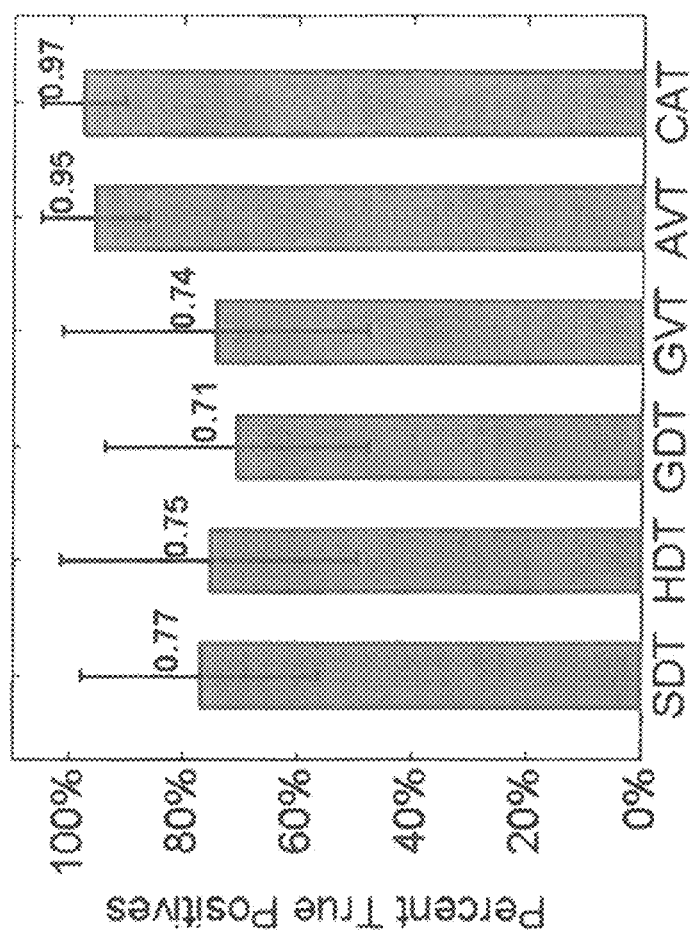
FIG. 10A-FIG. 10D show graphs of accuracy, false positive rate, duty cycle deviation, and resulting CS scores for the algorithm shown in FIG. 6 compared to five additional algorithms.
Figure 10B:
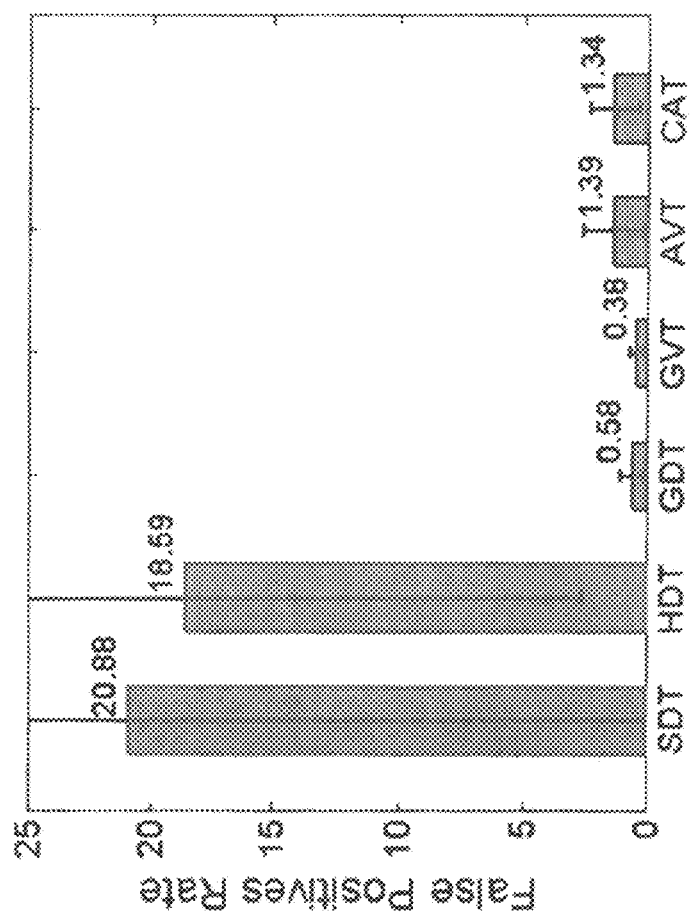
Figure 10C:
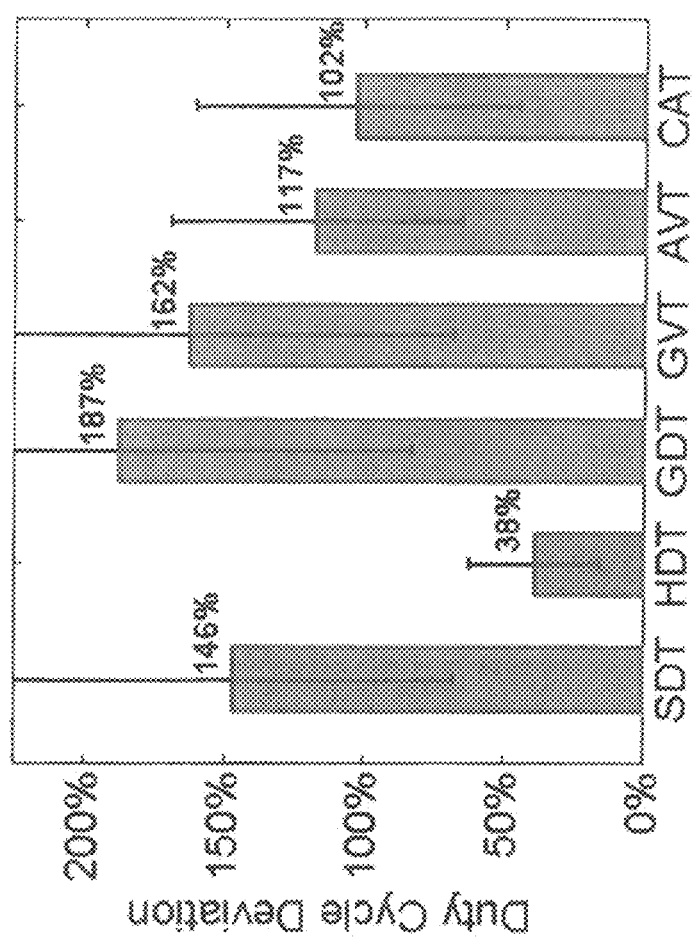
Figure 10D:
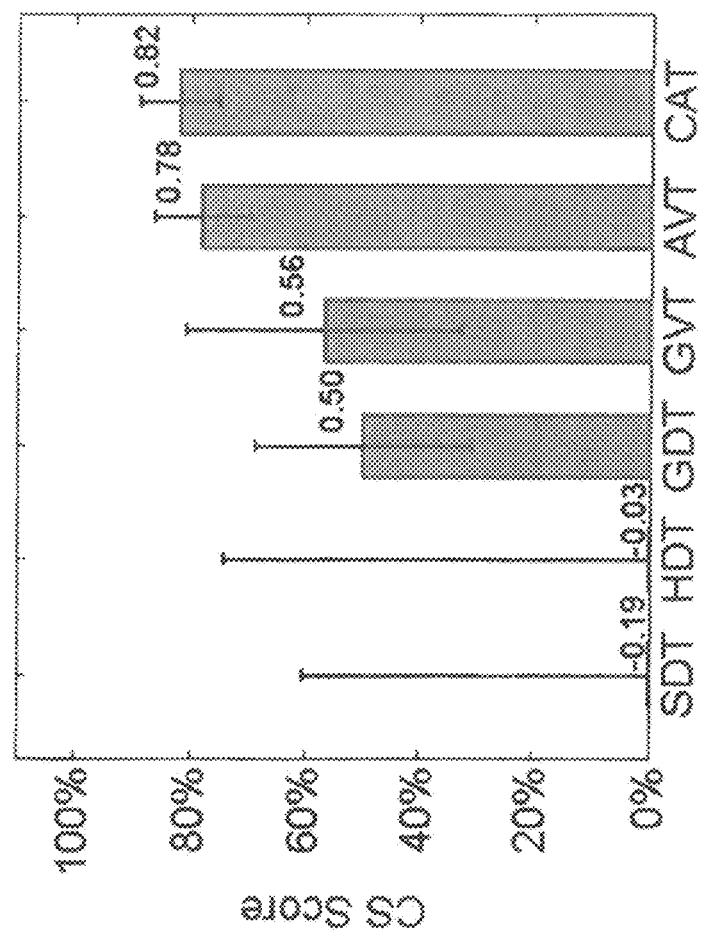

FIG. 9 shows sample outputs from the CAT algorithm, specifically contraction detection (FIG. 9(a)) well before the contraction onset or leak point pressure (dashed line) and artifact detection (FIG. 9(b)), which were not classified as contractions due to the higher rate of pressure increase. Finally, FIG. 9(c) gives an example of the denoising capabilities of wavelets, which demonstrates how adaptive thresholding in the wavelet domain can improve the specificity of the detection algorithm.

Algorithm Comparisons

Three static methods (SDT, GDT, GVT) were tested using different threshold values. With SDT, the same threshold of 10 cmH20 was used for each urodynamic tracing, while GDT and GVT were both tuned to individuals. Similarly, three adaptive methods (HDT, AVT, CAT) were tested. Algorithms were compared, testing the contraction detection rate, false positive rate, duty cycle deviation, and overall CS Score (FIG. 10). Results for both individualized and global tuning are summarized in Tables II and III.

TABLE II

Summary of Results for Individualized Tuning

| Type | Method | True Pos. (%) | False Pos. | Score |
|---|---|---|---|---|
| Static | SDT | 0.76 ± 0.2 | 21.6 ± 22.5 | −0.19 ± 0.8 |
| | GDT | 0.70 ± 0.2 | 0.6 ± 0.5 | 0.50 ± 0.2 |
| | GVT | 0.74 ± 0.3 | 0.4 ± 0.3 | 0.56 ± 0.2 |

TABLE II-continued

Summary of Results for Individualized Tuning

| Type | Method | True Pos. (%) | False Pos. | Score |
|---|---|---|---|---|
| Hybrid Adaptive | HDT | 0.75 ± 0.3 | 18.6 ± 15.9 | −0.03 ± 0.8 |
| | AVT | 0.85 ± 0.1 | 1.4 ± 1.3 | 0.78 ± 0.1 |
| | CAT | 0.97 ± 0.1 | 1.3 ± 1.0 | 0.82 ± 0.1 |

TABLE III

Summary of Results with Global Tuning

| Type | Method | True Pos. (%) | False Pos. (%) | Score |
|---|---|---|---|---|
| Static | SDT | 0.76 ± 0.2 | 21.6 ± 22.5 | −0.19 ± 0.8 |
| | GDT | 0.88 ± 0.3 | 2.26 ± 2.4 | 0.51 ± 0.3 |
| | GVT | 0.90 ± 0.3 | 2.04 ± 2.4 | 0.51 ± 0.3 |
| Hybrid Adaptive | HDT | 0.75 ± 0.3 | 18.6 ± 15.9 | −0.03 ± 0.8 |
| | AVT | 0.81 ± 0.4 | 8.10 ± 7.9 | 0.65 ± 0.3 |
| | CAT | 0.96 ± 0.2 | 9.21 ± 7.3 | 0.75 ± 0.2 |

As a hybrid of static and adaptive methods, HDT did not perform significantly better than either of the static methods, despite having a moving threshold. Conversely, AVT and CAT both demonstrated significant improvements in detection accuracy (95% and 97%, respectively) over static methods, though the false positive rates increased slightly when compared with GDT and GVT. For most tracings, operating in the wavelet domain resulted in fewer false positives while maintaining a high degree of accuracy.

Figure 11:
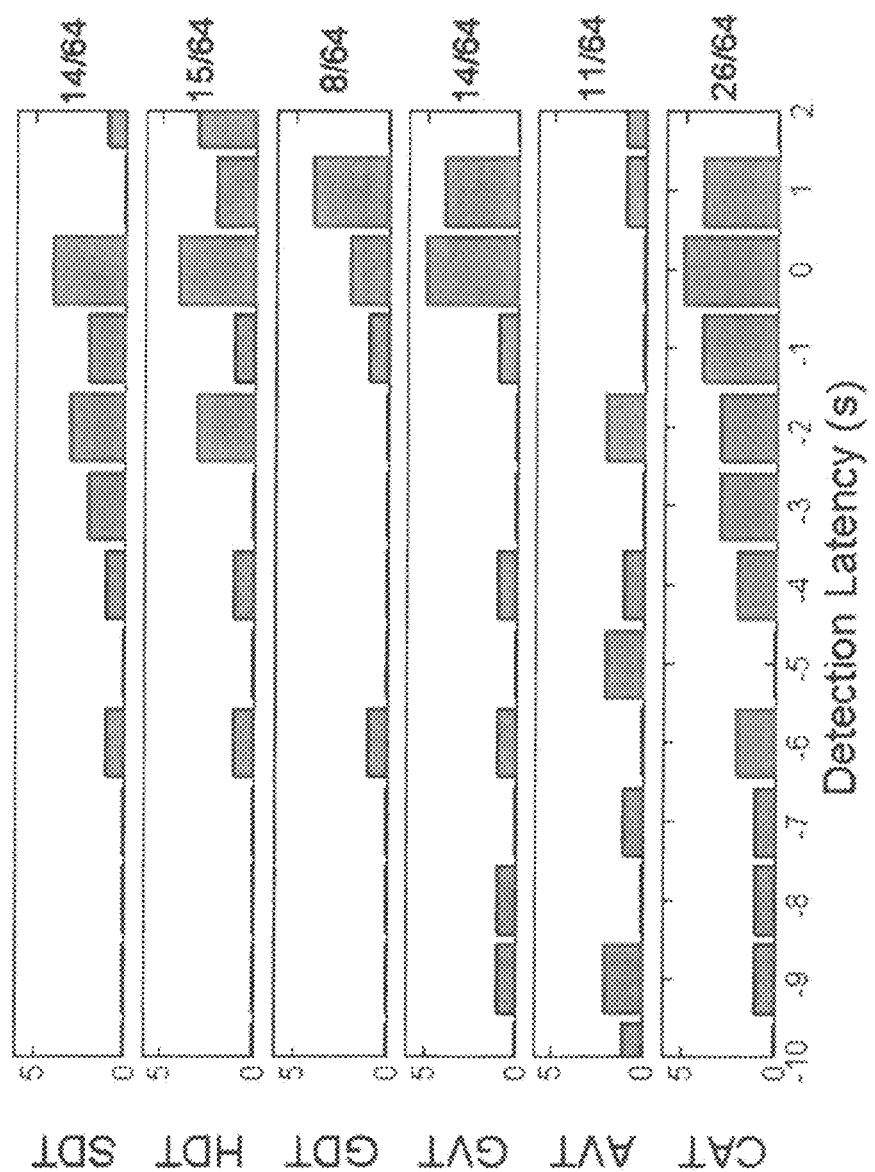
FIG. 11 shows graphs of detection latencies of the algorithm shown in FIG. 6 compared to five additional algorithms.

From a latency perspective, the CS Score accounts only for whether or not detection occurred within 1 second of contraction; the precise latency is not used for scoring. Therefore, it is important to note the differences in detection latency between the algorithms, as shown in FIG. 11 for a subset of detections. Note that negative latencies represent detection prior to contraction onset. CAT is more likely to detect contraction onset a short time in advance, reducing the possibility of overstimulation.

Using Tukey's pairwise comparisons, we found that a significant difference existed between the two methods not tuned to individuals (SDT, HOT) and the four that were (GDT, GVT, AVT, and CAT). Among tuned methods, a significant difference existed between the two purely static methods (GDT, GVT) and the purely adaptive methods (AVT, CAT). From this, we concluded that tuning the algorithm to an individual can improve performance even for a static method. Compared with AVT, the addition of the DWT improves CAT by providing two signal outputs for event detection, reducing the occurrence of false positives, and allowing for more efficient hardware implementation.

From the above description, those skilled in the art will perceive improvements, changes and modifications. Such improvements, changes and modifications are within the skill of one in the art and are intended to be covered by the appended claims.

What is claimed is:

1. A system comprising:
   a non-transitory memory storing instructions; and
   a processor to execute the instructions stored in the memory to at least:
      filter a signal indicating a pressure detected within a patient's bladder with a low-pass filter with a cutoff frequency tuned for the patient to provide a filtered signal, wherein the pressure detected within the patient's bladder is detected by a sensing device configured to be positioned within the patient's bladder and to send the signal indicating the pressure detected;

apply a multi-level discrete wavelet transform to the filtered signal to provide a transformed signal in a wavelet domain;

apply an adaptive thresholding procedure to the transformed signal in the wavelet domain to detect a bladder event, and characterize the bladder event as a voiding contraction event, a non-voiding contraction event, or a non-contraction event based on at least one property of the bladder event according to one or more tunable parameters customized for the patient.

2. The system of claim 1, further comprising the sensing device, wherein the sensing device comprises a circuit comprising a bridge-type pressure sensor adapted to directly detect the pressure within the patient's bladder.

3. The system of claim 2, wherein the sensing device is configured to be within the patient's bladder.

4. The system of claim 2, wherein the sensing device further comprises a wireless transceiver adapted to transmit the signal indicating the pressure within the patient's bladder.

5. The system of claim 2, wherein the sensing device further comprises a battery adapted to provide power to the bridge-type pressure sensor.

6. The system of claim 1, wherein the memory and the processor are embodied in a signal processing device.

7. The system of claim 6, wherein the signal processing device further comprises a wireless transceiver adapted to receive the signal indicating the pressure detected within the patient's bladder.

8. The system of claim 6, wherein the signal processing device is adapted to be implantable within the patient or external to the patient.

9. The system of claim 6, wherein the signal processing device is an application-specific integrated circuit (ASIC), an embedded circuit running software, a custom programmable hardware, or software on a hardware computing device.

10. The system of claim 1, wherein the bladder event is characterized as the non-contraction event based on a correlation between the pressure detected and another signal from an external sensor.

11. A method comprising: receiving, by a signal processing device comprising a processor, a signal indicating a pressure detected within a patient's bladder from a sensing device;

applying, by the signal processing device, a low pass filter to the signal with a cutoff frequency to remove noise from the signal, wherein the cutoff frequency is tuned for the patient;

applying, by the signal processing device, a multi-level discrete wavelet transform to the filtered signal to provide a transformed signal in a wavelet domain;

applying, by the signal processing device, an adaptive thresholding procedure to the transformed signal in the wavelet domain to detect a bladder event; and characterizing the bladder event as a voiding contraction event, a non-voiding contraction event, or a non-contraction event.

12. The method of claim 11, wherein the signal indicating the pressure is transmitted from the sensing device, wherein the sensing device is positioned within the patient's bladder.

13. The method of claim 12, wherein the sensing device comprises a circuit comprising a bridge-type pressure sensor adapted to directly detect the pressure within the patient's bladder.

14. The method of claim 12, wherein the sensing device comprises a wireless transceiver adapted to transmit the signal indicating the pressure within the patient's bladder.

15. The method of claim 12, wherein the sensing device comprises a battery adapted to provide power to the pressure sensor.

16. The method of claim 11, wherein the bladder event is characterized as the non-contraction event based correlating the pressure detected and another signal from an external sensor.

17. The method of claim 11, further comprising customizing the one or more tunable parameters for the patient.

18. The method of claim 11, further comprising continuously applying the adaptive thresholding procedure to detect additional bladder events.

19. The method of claim 18, wherein the adaptive thresholding procedure is updated with new parameters specific to the patient based on the characterizing the bladder event.

20. The method of claim 18, wherein the characterizing the bladder event is based on a value that is continually recomputed.

* * * * *